(12) United States Patent
Karjalainen et al.

(10) Patent No.: US 7,728,147 B2
(45) Date of Patent: Jun. 1, 2010

(54) DETOMIDINE HYDROCHLORIDE CRYSTALLIZATION METHOD

(75) Inventors: Arto Karjalainen, Espoo (FI); Seppo Parhi, Oulu (FI)

(73) Assignee: Orion Corporation, Espoo (FI)

( * ) Notice: Subject to any disclaimer, the term of this patent is extended or adjusted under 35 U.S.C. 154(b) by 183 days.

(21) Appl. No.: 11/911,181

(22) PCT Filed: Apr. 13, 2006

(86) PCT No.: PCT/FI2006/000113

§ 371 (c)(1),
(2), (4) Date: Jun. 2, 2008

(87) PCT Pub. No.: WO2006/108910

PCT Pub. Date: Oct. 19, 2006

(65) Prior Publication Data

US 2008/0287685 A1 Nov. 20, 2008

(30) Foreign Application Priority Data

Apr. 15, 2005 (FI) .................................. 20050391

(51) Int. Cl.
*C07D 233/58* (2006.01)
(52) U.S. Cl. .................................................. 548/346.1
(58) Field of Classification Search ........................ None
See application file for complete search history.

(56) References Cited

U.S. PATENT DOCUMENTS 4,584,383 A    4/1986    Parhi

OTHER PUBLICATIONS

Davey, DD. et al. "Convenient Synthesis of 4-methylhistamine and racemic alpha, 4-dimethylhistamine and alpha, 4-dimethylhistidine," *Journal of Organic Chemistry* (1989) 54(13):3211-3213.
International Search Report mailed Aug. 4, 2006, for International Application No. PCT/FI2006/000113.
Written Opinion mailed Jul. 4, 2006, for International Application No. PCT/FI2006/000113.

*Primary Examiner*—Kamal A Saeed
(74) *Attorney, Agent, or Firm*—Finnegan, Henderson, Farabow, Garrett & Dunner, LLP

(57) ABSTRACT

A method of isolating detomidine (I) hydrochloride as a crystalline salt is provided. The method comprises hydrogenating in the presence of a catalyst of compound of formula (II) in aqueous solution comprising hydrochloric acid, concentrating the solution by distillation, optionally adding hydrochloric acid to the concentrated solution, cooling the concentrated solution and recovering the crystallized detomidine hydrochloride. The product can be recovered directly from aqueous solution with

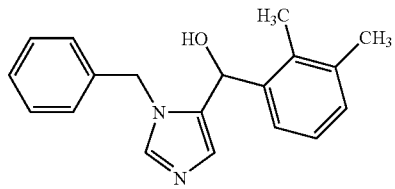

(II)

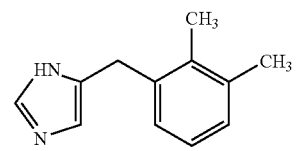

(I)

15 Claims, No Drawings

DETOMIDINE HYDROCHLORIDE CRYSTALLIZATION METHOD

This application is a national stage filing under 35 U.S.C. § 371 of International Application No. PCT/FI2006/000113, filed on Apr. 13, 2006, which claims the benefit of priority of Finnish Application No. 20050391, filed on Apr. 15, 2005, the contents of each application are incorporated herein by reference.

FIELD OF THE INVENTION

The present invention relates to a method of preparing detomidine hydrochloride. Particularly the present invention relates to an improved method of isolating detomidine hydrochloride as crystalline salt.

BACKGROUND OF THE INVENTION

Detomidine which is 4-[(2,3-dimethylbenzyl)]imidazole of formula I

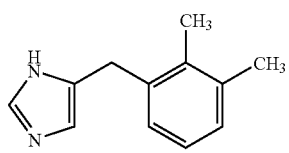

is a well known pharmaceutical agent currently used as its hydrochloride salt in animal sedation.

The synthesis of detomidine is described in U.S. Pat. Nos. 4,443,466 and 4,584,383. The preparation of detomidine hydrochloride salt is described in U.S. Pat. No. 4,584,383, wherein detomidine obtained from the hydrogenation step is first recovered from alkaline solution as a free base after which the crystalline product is converted into its hydrochloride salt by treatment with HCl-isopropanol in ethyl acetate.

SUMMARY OF THE INVENTION

The present invention is directed to an improved method of isolating detomidine hydrochloride salt. The novel method is more efficient and economical than the methods previously disclosed. In particular, the method of the present invention provides crystalline detomidine hydrochloride directly without the need to isolate detomidine base. Furthermore, the use of isopropanol and ethylacetate solvents is avoided, as crystalline detomidine hydrochloride can be obtained directly from its aqueous solution.

DETAILED DESCRIPTION OF THE INVENTION

The present invention provides a method for preparing detomidine hydrochloride wherein the method comprises
a) hydrogenation under catalyst of compound of formula (II) or a salt thereof

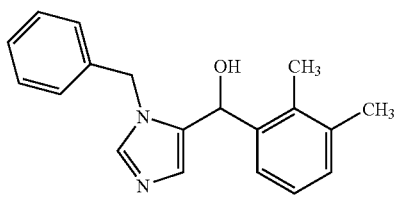

in aqueous solution comprising hydrochloric acid;
b) concentrating the solution by distillation;
c) optionally adding hydrochloric acid to the concentrated solution;
d) cooling the concentrated solution, and
e) recovering the crystallized detomidine hydrochloride.

The hydrogenation of compound (II) is suitably performed in aqueous solution comprising hydrochloric acid. The amount of hydrochloric acid is suitably from about 0.5 to about 5%, preferably from about 1 to about 3%, for example from about 1.5 to about 2.5%, per total weight of the aqueous solution.

The weight ratio of compound (II) to the solvent of aqueous solution is preferably from about 1:7 to about 1:30, more preferably from about 1:8 to about 1:20, for example from about 1:9 to about 1:15. Preferably, at least about 90%, more preferably at least about 95%, per weight of the solvent of aqueous solution is water. Advantageously, the aqueous solution contains from about 0.1 to about 10% per weight, preferably from about 0.5 to about 5% per weight, for example from about 1 to about 3% per weight, of lower alcohol, preferably ethanol. The hydrogenation is suitably performed in the presence of a catalyst under hydrogen atmosphere at normal or elevated hydrogen pressure. Suitable catalysts include palladium, platinum, Raney-nickel and platinum oxide. Palladium or platinum is conveniently used on a carrier such as charcoal. Palladium-on-charcoal is the preferred catalyst. Reaction is conducted at normal or elevated temperature, for example at 25-100° C., preferably at 60-80° C., for a period until the hydrogenation reaction is finished. Typical reaction time is about 20-40 hours. After the hydrogenation, the mixture is preferably cooled and filtered.

In the next step the aqueous filtrate solution containing detomidine is concentrated. This is performed suitably by distilling off part of the solvent under reduced pressure. Preferably, the solution is concentrated by distilling off from about 50 to about 85% per weight, more preferably from about 60 to about 80% per weight, for example from about 65 to 75% per weight, of the total amount of solvent present in the solution.

If necessary, hydrochloric acid may be added to the concentrated solution to obtain the desired hydrochloric acid concentration for crystallizing detomidine hydrochloride upon cooling of the solution. Preferably, the concentrated solution from which the crystallization is carried out comprises from about 2% to about 15%, more preferably from about 4% to about 10%, for example from about 5% to about 8%, per weight of hydrochloric acid.

The crystallization of detomidine hydrochloride is suitably carried out by cooling the solution to a temperature which is lower than 20° C., preferably lower than 15° C., more preferably lower than 10° C., and especially lower than 7° C. It is particularly preferred to carry out crystallization by cooling the solution to a temperature which is from about 0° C. to about 6° C., for example about 3° C.

The cooling is preferably carried out during 0.5 to 10 hours, typically during 1 to 3 hours, for example during 2 hours. The solution is preferably agitated in the crystallization temperature, preferably from 0.5 to 5 hours, typically from 1 to 3 hours. If desired, the solution can be seeded with detomidine hydrochloride crystals during the cooling process until the crystallization starts. This can be performed stepwise at various temperatures during cooling, e.g. by adding seeding crystals at 40° C., 30° C., 20° C. and 10° C., until the crystallizations starts.

The crystalline product can be recovered from the solution by conventional methods such as centrifugation or filtering. The crystalline product can be washed with suitable solvent and dried at elevated temperature. Suitably, the wet product is dried in vacuum at about 35-90° C. for 24-50 hours.

If desired, the product can be recrystallized by repeating the above crystallization step, e.g. by dissolving the product into water by warming, distilling off part of the water solvent, adding hydrochloric acid, cooling and recovering the recrystallized product.

The following example is used to illustrate but by no means to limit the scope of the invention, which is defined in the claims.

EXAMPLE 1

Preparation of 4-[(2,3-dimethylbenzyl)]imidazole hydrochloride (detomidine HCl)

1-Benzyl-5-(2,3-dimethylphenylhydroxymethyl)imidazole (20 kg), water (225 l), 30% HCl (20 l), ethanol (5 l) and palladium on charcoal 10% (4.4 kg) are charged. The mixture is stirred under 2.2 bar overpressure of hydrogen at 75±5° C. for 24 hours. The reaction mixture is filtered at 45±3° C. and the filter cake is washed with water (30 l). 170 l of water is distilled off under reduced pressure and 30% HCl (8 l) is added. The solution is cooled to 3±3° C. during 2 h. The solution is seeded with crystals of detomidine HCl at 40±5° C., 30±5° C., 20±5° C. and at 10±5° C., until the crystallization starts. The mixture is agitated for two hours. The crystalline compound is collected by centrifugation and washed with toluene. The crude product and water (250 l) are charged. The solution is heated to about 50° C. and stirred for 1 hour. The solution is cooled to 10° C. during 1.5 hour. The solution is filtered and 180 l of water is distilled off under vacuum. 30% HCl (20 l) is added and the solution is warmed to 60° C., and then cooled to 3±3° C. during 2 hours. The solution is seeded as above until the crystallization starts and agitated for two hours. The crystalline compound is collected by centrifugation and washed with toluene. The product is dried under vacuum at 39±5° C. for 20 hours, at 61±5° C. for 6 hours and at 85±5° C. for 16 hours. The yield is 10.5 kg (78%).

The invention claimed is:

1. A method for preparing detomidine hydrochloride comprising
   a) hydrogenating in the presence of a catalyst of compound of formula (II) or a salt thereof

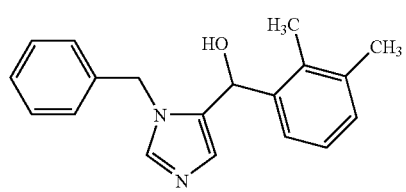

(II)

in an aqueous solution comprising hydrochloric acid;

b) concentrating the solution obtained in step a) by distillation;
   c) optionally adding hydrochloric acid to the concentrated solution obtained in step b);
   d) cooling the concentrated solution, and
   e) recovering the crystallized detomidine hydrochloride.

2. A method according to claim 1, wherein at least about 90% per weight of the aqueous solution is water.

3. A method according to claim 2, wherein at least about 95% per weight of the aqueous solution is water.

4. A method according to claim 1, wherein the aqueous solution comprises from 0.1 wt % to 10 wt % of lower alcohol.

5. A method according to claim 4, wherein the lower alcohol is ethanol.

6. A method according to claim 1, wherein the weight ratio of compound (II) to the aqueous solution is from about 1:7 to about 1:30.

7. A method according to claim 6, wherein the weight ratio of compound (II) to the aqueous solution is from about 1:8 to about 1:20.

8. A method according to claim 1, wherein the solution obtained in step a) is concentrated by distilling off from about 50% to about 85% per weight of the total amount of the aqueous solution.

9. A method according to claim 8, wherein the solution obtained in step a) is concentrated by distilling off from about 60% to about 80% per weight of the total amount of the aqueous solution.

10. A method according to claim 1, wherein the concentrated solution obtained in step b) comprises from about 2% to about 15% per weight of hydrochloric acid.

11. A method according to claim 10, wherein the concentrated solution obtained in step b) comprises from about 4% to about 10% per weight of hydrochloric acid.

12. A method according to claim 1, wherein the concentrated solution obtained in step b) is cooled to a temperature which is lower than 10° C.

13. A method according to claim 12, wherein the concentrated solution obtained in step b) is cooled to a temperature which is from about 0° C. to about 6° C.

14. A method according to claim 1, wherein the cooling is carried out for 0.5 hours to 10 hours.

15. A method according to claim 14, wherein the cooling is carried out for 1 hour to 3 hours.

* * * * *

UNITED STATES PATENT AND TRADEMARK OFFICE
CERTIFICATE OF CORRECTION

PATENT NO. : 7,728,147 B2
APPLICATION NO. : 11/911181
DATED : June 1, 2010
INVENTOR(S) : Arto Karjalainen et al.

It is certified that error appears in the above-identified patent and that said Letters Patent is hereby corrected as shown below:

On the Title Page, Item (57), in the Abstract, line 9, "solution with" should read
--solution without the need to isolate detomidine base. Detomidine (I) and Formula (II).--

Signed and Sealed this

Thirteenth Day of July, 2010

David J. Kappos
*Director of the United States Patent and Trademark Office*